United States Patent [19]

Munson, Jr. et al.

[11] Patent Number: 5,171,753

[45] Date of Patent: Dec. 15, 1992

[54] DERIVATIVES OF 2-AMINO-1-PHENYLETHANOL HAVING ANTIULCER ACTIVITY

[75] Inventors: Harry R. Munson, Jr., Leawood, Kans.; Robert F. Boswell, Richmond, Va.

[73] Assignee: A. H. Robins Company, Incorporated, Richmond, Va.

[21] Appl. No.: 700,657

[22] Filed: May 15, 1991

[51] Int. Cl.$^5$ ............... A61K 31/135; A61K 31/495; C07C 215/34; C07D 295/13

[52] U.S. Cl. .................. 514/653; 514/255; 514/651; 514/926; 514/927; 544/401; 564/346; 564/363; 564/364; 564/365

[58] Field of Search ............... 564/363, 364, 365, 346; 514/649, 926, 927, 92, 653, 651, 255; 544/401

[56] References Cited

U.S. PATENT DOCUMENTS

| | | | |
|---|---|---|---|
| 2,884,459 | 4/1959 | Kirkpatrick, II | 564/363 |
| 3,152,188 | 10/1964 | Kirkpatrick, I | 564/363 |
| 3,928,621 | 12/1975 | Boris | 424/330 |
| 4,618,624 | 10/1986 | Asato | 514/486 |
| 4,723,039 | 2/1988 | Seitz et al. | 564/344 |
| 4,803,200 | 2/1989 | Munson, Jr. et al. | 514/231.2 |

FOREIGN PATENT DOCUMENTS

| | | |
|---|---|---|
| 816519 | 6/1973 | Belgium . |
| 0103830 | 3/1984 | European Pat. Off. ........ 564/365 |
| 225415A | 2/1988 | European Pat. Off. . |
| 288867A | 2/1988 | European Pat. Off. . |
| 2261914 | 6/1979 | Fed. Rep. of Germany . |
| 52-105138 | 9/1977 | Japan . |

OTHER PUBLICATIONS

J. Amer. Chem. Soc., 70, 2015-2023 (1948).
J. Amer. Chem. Soc., 71, 478-481 (1949).

*Primary Examiner*—Richard L. Raymond
*Assistant Examiner*—P. O'Sullivan
*Attorney, Agent, or Firm*—Robert F. Boswell, Jr.

[57] ABSTRACT

Derivatives of 2-amino-1-phenylethanol were prepared from substituted amines and benzoin, stilbene oxide or styrene oxide to give compounds of Formula:

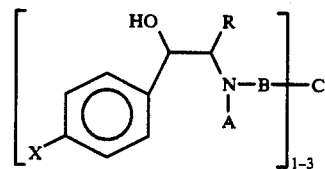

where R is H or (un)substituted phenyl and C is a linking group or terminal group. The compounds of this invention can inhibit ulceration in in-vivo studies in rats.

5 Claims, No Drawings

DERIVATIVES OF 2-AMINO-1-PHENYLETHANOL HAVING ANTIULCER ACTIVITY

Field of Invention

Certain derivatives of 2-amino-1-phenylethanol have been found to have antiulcer activity in ethanol-induced gastric ulceration and Dulcerozine induced duodenal ulceration studies in laboratory rats. It is therefore an object of this invention to provide a method of treating ulcers and to provide a pharmaceutical composition therefor. Compounds of this invention incorporating two to three 2-amino-1-phenylethanol groups linked by a chain of at least 2 atoms are novel.

BACKGROUND OF THE INVENTION

U.S. Pat. No. 4,803,200 discloses antiviral activity of derivatives of 2-amino-1-phenylethanols, some compounds of which are useful in the method and pharmaceutical composition of this invention. Some of the invention compounds were described in J. Amer. Chem. Soc. 70, 2015-2023 (1948) as having antitumor properties. Antiinflammatory activity was reported for some 2-(aminoalkylamine)-1,2-diphenylethanols in U.S. Pat. No. 3,928,621. Antiiflammatory activity and improvement in animal growth and productivity is also reported for 2-amino-1-(4-aminophenyl)ethanol derivatives in EP 288867A. Other biological activities reported for variously substituted 2-amino-1-phenylethanol derivatives include treatment of gastrointestinal disorders caused by smooth muscle contractions (EP 255415A), improved feed efficiency (U.S. Pat. No. 4,618,624), cardiovascular agents (Belgian 866401), bronchodilating agents (Japan 52105138), adrenergic stimulants (German 2551945), and beta-adrenergic agents (Belgian 816419, Netherlands 7316139 and Dutch 2261914).

SUMMARY OF THE INVENTION

The compounds useful in the method and composition of this invention are represented by Formula I.

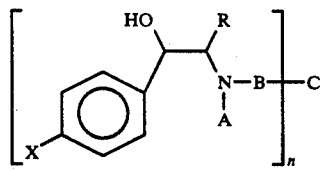

Formula I

Under Formula I, X is H, —Cl, —CH$_3$, or —OCH$_3$;
A is —H, —CH$_3$ or

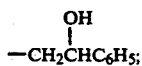
—CH$_2$CHC$_6$H$_5$;

n is 1 to 3;
B is C$_1$-C$_6$ alkylene, optionally substituted with —OH, —CH$_2$OH, or —CH$_3$ or A and B together with the interposed nitrogen forms a piperidine ring substituted at the 4 position by a substituent according to C or B is a bond between N and C;
C is a terminal group when n is 1 selected from the group consisting of —H, —OH, —SH, —NH$_2$, —O—(C$_1$-C$_6$ alkyl), —S—(C$_1$-C$_6$ alkyl), —O—(CH$_2$)$_{2-6}$—OH, —O—(CH$_2$)$_{2-6}$—O—(C$_1$-C$_6$ alkyl), —CH(OCH$_3$)$_2$, —OCH$_2$C$_6$H$_5$, —CO$_2$C$_2$H$_5$, phenyl, (C$_1$-C$_6$ alkyl)$_2$N—,

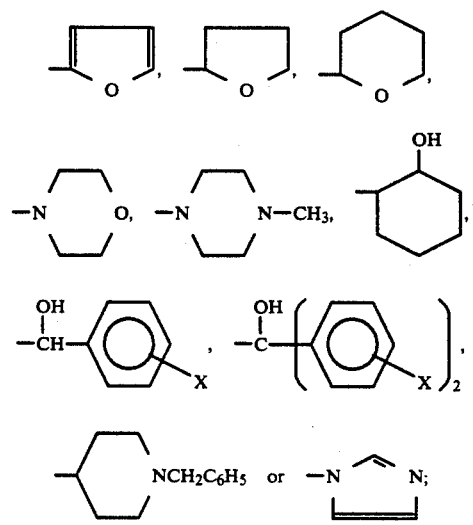

or when n is 2 or 3, C is a linking group selected from the group consisting of

—O—(CH$_2$)$_{2-6}$—O—, —O—, —S—, —CH(OH)—,

—N(CH$_3$)—, —N|—, —N\_/N—, or —(CH$_2$)$_{1-6}$—;

R is H or

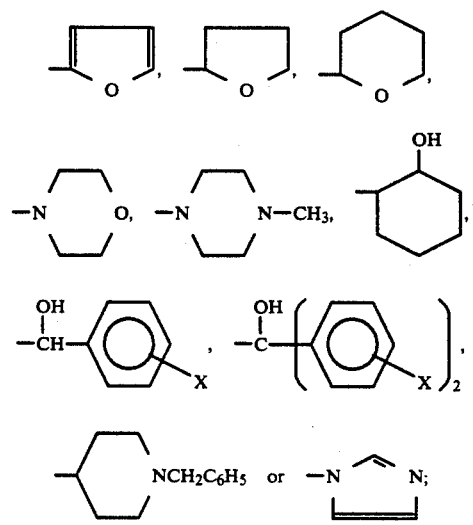

where X is as defined above.

Also encompassed under Formula I are the optical isomers and diastereomers and the pharmaceutically acceptable salts, which include hydrates, solvates, and acid addition salts. Acid addition salts are those salts formed between the base of a Formula I compound and a pharmaceutically acceptable acid including hydrochloric acid, hydrobromic acid, sulfuric acid, phosphoric acid, maleic acid, fumaric acid, succinic acid, citric acid, tartaric acid, ethanesulfonic acid, cyclohexylsulfamic acid, pamoic acid and the like. The C$_1$-C$_6$ alkyl groups in the above definitions can be straight or branched and are exemplified by methyl, ethyl, propyl, isopropyl, butyl, t-butyl, isobutyl, pentyl, hexyl and the like.

Antiulcer compounds can inhibit the formation of ulcers induced in the stomach by administration of absolute ethanol or those induced in the duodenum by administration of Dulcerozine and Meperizole, depending on their mechanism of action. Meperizole, structurally similar to Dulcerozine, also induces duodenal ulcers [Tanaka et al., Digestive Diseases and Science 34(2), 238-245 (1989)]. A combination of Dulcerozine and Meperizole given orally produced more consistent duodenal ulcer formation than Dulcerozine alone. Formula I compounds of this invention are useful in reducing ulcer formation. Compounds which inhibit ulcer formation in one of these tests may not inhibit ulcer formation in the other test due to differing mechanisms of action at the two different sites of ulceration.

DETAILED DESCRIPTION OF THE INVENTION

The Formula I compounds are prepared by heating together an amine and an epoxide (Scheme A), i.e., a stilbene oxide or styrene oxide, or an amine and a benzoin followed by reduction (Scheme B).

Scheme A

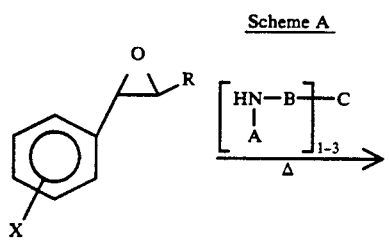

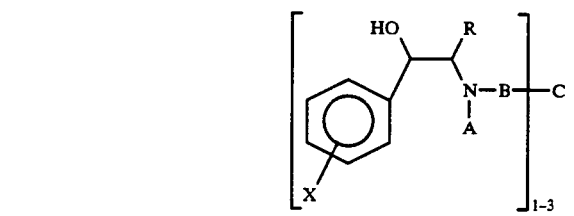

The epoxide and amine are heated together neat, with triethyl amine added to liberate amines from amine salts, at from 100° to 150° C. When the amine contains 2 or 3 primary amino groups, excess epoxide must be used to minimize formation of mixture of products.

After the reaction is completed the crude product is either triturated in an appropriate solvent such as isooctane and recrystallized from tolueneisooctane mixture, dissolved in methanol and poured into water from which the product crystallizes or separates as an oil from which a salt can be formed, or the product is dissolved in a solvent such as ethanol and treated with an anhydrous acid to form a salt.

Where R is

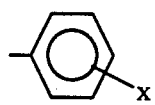

and the epoxide is of the trans configuration, the product obtained is a diastereomer having the erythro conformation. When R is

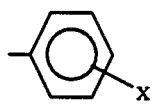

and the epoxide is of the cis configuration, the product obtained has the threo configuration.

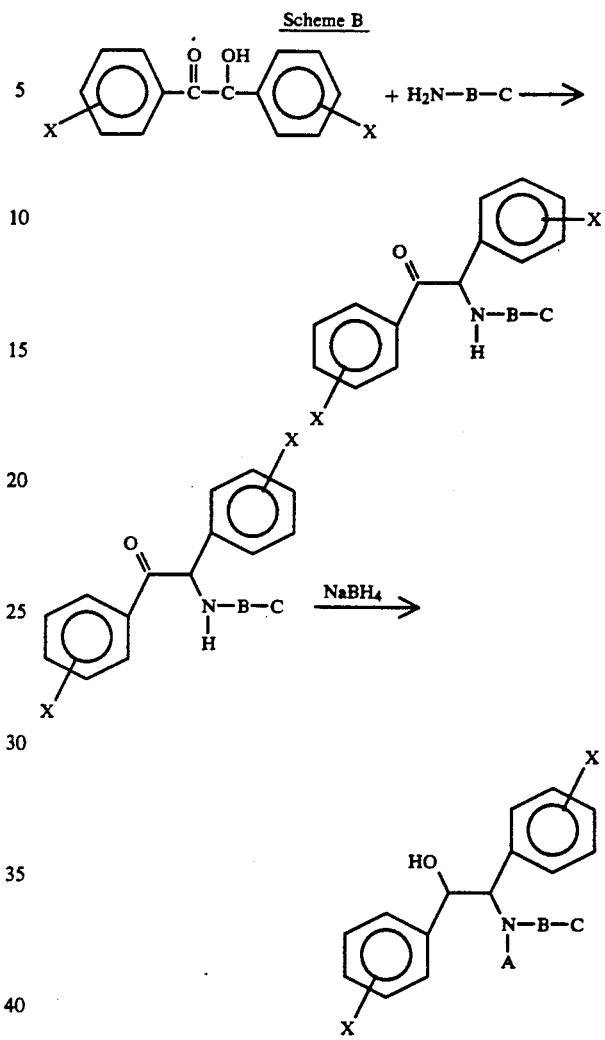

Under Scheme B, the benzoin and amine are heated together neat, sometimes with a catalytic amount of phosphorus pentoxide, at from 100° C. to 150° C. and the resulting ketone reduced, often without isolation, with a reducing agent such as sodium borohydride. The Formula I compounds obtained by Scheme A or B were isolated and purified using standard laboratory techniques.

The Formula I compounds where n is 2 or 3 are novel and are prepared by reacting a di- or tri-amine, where the amino groups are separated by 2 or more atoms, with excess amounts of a stilbene oxide or styrene oxide. It is expected that the reaction according to Scheme B would also give Formula I compounds where n is 2 or 3 when excess benzoin is reacted with said di- or triamine.

The amines, benzoins and epoxides used are available from commercial sources or prepared according to published procedures. The following Preparations and Examples are included for illustrative purposes only and are not limiting to the scope of this invention in any way. Other methods of preparation will be obvious to one skilled in the art.

Preparation 1

2,3-Bis-(4-chlorophenyl)oxirane trans isomer.

This intermediate is prepared according to the procedures given in J. Amer. Chem. Soc. 71, 478 (1949).

Preparation 2

4,4'-dimethylbenzion.

A mixture of tolualdehyde (40.0 g, 0.33 mol), ethanol (20%) and KCN (10.84 g, 0.17 mol) was heated at reflux temperature for 18 hours. Additional KCN (10.84 g, 0.17 mol) was added and reflux continued for another 5 hours. Aqueous sodium bisulfite was added and the mixture allowed to cool. The mixture was extracted with methylene chloride and the extract concentrated. The residue crystallized on trituration with 2-propanol to yield 14.26 g (35% yield).

EXAMPLE 1

2-[(2-hydroxy-1,2-diphenylethyl)amino]acetic acid ethyl ester.

A stirred mixture of trans-stilbene oxide (6.48 g, 0.033 mol), and glycine ethyl ester (6.15 g, 0.0598 mol) was heated at 120° for 22 hours. The mixture was triturated with ether and filtered to remove some insoluble materials. The filtrate was concentrated to yield 6.83 g (69.1%) of oil which solidified into a waxy solid upon cooling. The compound was purified and characterized as the hydrochloride salt, mp 185°–187° C. (absolute ethanol/isopropyl ether) [reported mp 167°, *Can. J. Chem.* 45, 2865 (1967)].

Analysis: Calculated for $C_{18}H_{22}NO_3Cl$: C, 64.38; H, 6.60; N, 4.17 Found: C, 64.11; H, 6.62; N, 4.25

EXAMPLE 2

2-Methyl-2-[(2-hydroxy-1,2-diphenylethyl)amino]-1,3-propanediol.

A mixture of trans-stilbene oxide (2.00 g, 0.010 mol) and 2-amino-2-methyl-1,3-propanediol (3.15 g, 0.030 mol) was heated at 150° C. for 3 hours. The reaction mixture was dissolved in 20 mL of methanol and diluted with water to form a white solid. The solid was collected, washed with water and dried for 18 hours under ambient conditions to obtain 2.46 g (82%) of the product. Recrystallization from toluene gave 2.38 g of material; mp 144°–145° C.

Analysis: Calculated for $C_{18}H_{23}NO_3$: C, 71.73; H, 7.69; N, 4.65 Found: C, 71.64; H, 7.71; N, 4.66

EXAMPLE 3

1-[[(2-Hydroxy-1,2-diphenylethyl)amino]methyl]-1,2-ethanediol.

A mixture of trans-stilbene oxide (3.93 g, 0.20 mol) and 1-amino-2,3-propanediol (5.46 g, 0.060 mol) was heated at 125° C. for 18 hours in an oil bath. After cooling, the reaction mixture was dissolved in 20 mL of methanol and the solution poured into 150 mL of water. The product separated from the solution as a viscous cream-colored oil that slowly solidified. The solid was collected by filtration and vacuum dried at 40° C. for 18 hours to give 3.81 g (66% yield) of material. The product was recrystallized from methanol-isopropyl ether to give 1.75 g; mp 161°–163° C.

Analysis: Calculated for $C_{17}H_{21}NO_3$: C, 71.06; H, 7.37; N, 4.87 Found: C, 71.02; H, 7.43; N, 4.90

EXAMPLE 4

2-[[(2-Hydroxy-1,2-diphenylethyl)amino]methyl]-1,4-butanediol.

A mixture of trans-stilbene oxide (1.96 g, 0.010 mol) and 2-aminomethyl-1,4-butanediol (2.63 g, 0.022 mol) was heated on a steam bath for 18 hours. The reaction mixture was dissolved in methanol (20 mL) and the solution poured into water (150 mL). The aqueous mixture was extracted with 2×75 mL of methylene chloride. The combined extract was dried ($MgSO_4$) and concentrated to give 2.60 g of a clear oil. After standing at ambient temperature for several hours there was evidence of crystallization occurring. The product was triturated with toluene (50 mL) to obtain the solid product. The mixture of product and toluene was heated to obtain a clear solution. After cooling and trituration, a white solid product was collected and dried under ambient conditions to obtain 1.79 g (57%); mp 80°–82° C.

Analysis: Calculated for $C_{19}H_{25}NO_3$: C, 72.35; H, 7.99; N, 4.44 Found: C, 72.09; H, 7.96; N, 4.49

Example 5

β-[[3-(diethylamino)-2-hydroxypropyl]amino]-α-phenylbenzeneethanol.

A mixture of trans-stilbene oxide (1.96 g, 0.010 mol) and 1-amino-2-hydroxy-3-(diethylaminopropane) (4.38 g, 0.030 mol) was heated in an oil bath at 100° C. for 18 hours. After standing at ambient temperature for 38 hours, the mixture was triturated with methanol, giving a white solid that was collected, washed with methanol and dried under ambient conditions for 2 hours to give 1.60 g of a white solid (47% yield). The solid was recrystallized from toluene to give 1.31 g of the product; mp 172°–173° C.

Analysis: Calculated for $C_{21}H_{30}N_2O_2$: C, 73.65; H, 8.83; N, 8.18 Found: C, 73.66; H, 8.99; N, 8.21

Example 6

α-[[(2-hydroxy-1,2-diphenylethyl)amino]methyl]-4-morpholinepropanol.

A mixture of trans-stilbene oxide (1.96 g, 0.010 mol) and 4-(4-amino-3-hydroxybutyl)morpholine (3.48 g, 0.020 mol) was heated on a steam bath for 18 hours. The resulting viscous oil was dissolved in methanol (20 mL) and the solution poured into water (150 mL). The aqueous mixture was extracted twice with 100 mL portions of methylene chloride. The extract was dried ($MgSO_4$) and concentrated to obtain 3.29 g of the impure product as an oil. The material was chromatographed on silica gel (60 g) using increasing portions of acetone in ethyl acetate to elute the product. After combining the desired fractions and concentration under vacuum, 2.21 g (67%) of the product was obtained. The product was purified and characterized as the cyclohexyl sulfamic acid salt, mp 159°–160° C. (methanol/isopropyl ether).

Analysis: Calculated for $C_{22}H_{30}N_2O_3 \cdot C_6H_{13}NO_3S$: C, 61.18; H, 7.88; N, 7.64 Found: C, 61.22; H, 7.96; N, 7.60

Example 7

2-[(2-hydroxy-1,2-diphenylethyl)amino]-1-phenyl-1,3-propanediol.

A mixture of trans-stilbene oxide (1.96, 0.010 mol) and 1R,2S(+)-2-amino-1-phenyl-1,3-propanediol (3.24 g, 0.020 mol) was heated in an oil bath at 100° C. for 18 hours. The mixture was then dissolved in methanol (20 mL) and the solution poured into water (100 mL). The mixture was extracted twice with 100 mL portions of methylene chloride. The combined extract was dried ($MgSO_4$) and concentrated to obtain 2.41 g of a clear viscous oil. TLC analysis (ethyl acetate) showed two main components. The material was chromatographed on silica gel (50 g) using increasing portions of ethyl acetate in toluene as eluants. An incomplete separation was achieved, but an NMR analysis indicated that the two components were diastereomers. The fractions were combined and concentrated to obtain 1.49 g (41% yield) of the diastereomer mixture. For characterization the product was converted to the hexamic acid salt which was isolated as the hemi-hydrate.

Analysis: Calc. for $C_{23}H_{25}NO_3 \cdot C_6H_{13}NO_3S \cdot 0.5H_2O$: C, 63.14; H, 7.13; N, 5.08 Found: C, 63.42; H, 7.29; N, 5.06

EXAMPLE 8

$\alpha,\alpha'$-[Iminomethylene(phenylmethylene)]bisbenzenemethanol.

A mixture of trans-stilbene oxide (2.44 g, 0.0125 mol) and 2-amino-1-phenylethanol (5.12 g, 0.0374 mol) was heated on a steam bath for 3 hours and allowed to stand at ambient temperature for 16 hours. Trituration with methanol-isopropyl ether gave a white solid (1.12 g, 77% yield). The solid was recrystallized from methanol-water to obtain 0.8 g of the product; mp 162°–163° C.

Analysis: Calculated for $C_{22}H_{23}NO_2$: C, 79.25; H, 6.95; N, 4.20 Found: C, 79.17; H, 7.06; N, 4.24

EXAMPLE 9

4-[Bis(4-fluorophenyl)hydroxymethyl]-$\alpha,\beta$-diphenyl-1-piperidinethanol.

A mixture of trans-stilbene oxide (1.96 g, 0.010 nmol) and 1,1-bis(4-fluorophenyl)-1-(4-piperidinyl)methanol (3.34 g, 0.011 mol) was heated at 150° C. in an oil bath for 2 hours. After standing at ambient temperature for 16 hours the mixture was dissolved in methanol (20 mL) and the solution poured into water (200 mL). The product separated from solution as a taffy-like mass that slowly solidified with trituration. The solid was collected and dried under ambient conditions for 18 hours to obtain 4.85 g (97% yield). The solid was recrystallized from isooctane to yield 3.20 g of a solid that was shown by nmr analysis to contain isooctane and this was not removed by vacuum drying. The solid product was converted to the hydrochloride salt, recrystallized from methanol/isopropyl ether and isolated as the hydrochloride hemihydrate; mp 242° C. (decomposes).

Analysis: Calc. for $C_{32}H_{31}NO_2F_2 \cdot HCl \cdot 0.5H_2O$: C, 70.52; H, 6.10; N, 2.57 Found: C, 70.44; H, 6.01; N, 2.72

EXAMPLE 10

$\alpha$-Phenyl-$\beta$-[(tetrahydrofuran-2-ylmethyl)amino]-benzeneethanol.

A mixture of trans-stilbene oxide (1.96 g, 0.010 mol) and tetrahydrofurfurylamine (3.03 g, 0.030 mol) was heated at 140° C. for 2 hours. After standing at ambient temperature for 18 hours the mixture was diluted with water (150 mL). An oil separated from the solution but solidified on standing for an hour. NMR and mass spectral analyses showed stilbene oxide remaining. The solid was treated with another 3.03 g of tetrahydrofurfurylamine and the mixture heated at 150° C. for another 3 hours. The reaction mixture was treated with water (150 mL) as before to obtain 2.28 g (77%) of an off-white solid after drying under ambient conditions for 18 hours. The solid was recrystallized form toluene; mp 167°–168° C.

Analysis: Calculated for $C_{19}H_{23}NO_2$: C, 76.74; H, 7.80; N, 4.71 Found: C, 76.74; H, 8.05; N, 4.69

EXAMPLE 11

$\beta$-[[3-(2-Ethoxyethoxy)propyl]amino]-$\alpha$-phenylbenzeneethanol.

A mixture of trans-stilbene oxide (1.96 g, 0.010 mol) and 3-[(2-ethoxy)ethoxy]-1-propylamine (4.41 g, 0.030 mol) was heated at 140° C. for 5 hours. The reaction mixture was dissolved in acetone (20 mL) and the solution poured into water (120 mL). The solid that formed was collected by filtration and dried under ambient conditions to give 3.0 g (87%) of material. Recrystallization from isooctane gave 2.45 g of the product; mp 65°–66° C.

Analysis: Calculated for $C_{21}H_{29}NO_3$: C, 73.44; H, 8.51; N, 4.08 Found: C, 73.43; H, 8.60; N, 4.12

EXAMPLE 12

$\beta$-[(2-Furanylmethyl)amino]-$\alpha$-phenylbenzeneethanol.

A mixture of trans-stilbene oxide (1.96 g, 0.010 mol) and furfurylamine (3.00 g, 0.030 mol) was heated at 140° C. for 6 hours, and then allowed to stand at ambient temperature for 14 hours. The solidified reaction mixture was triturated with petroleum ether and the crude solid collected by filtration. Recrystallization from toluene-isooctane gave 2.3 g (78%) of the product; mp 141°–144° C.

Analysis: Calculated for $C_{19}H_{19}NO_2$: C, 77.79; H, 6.53; N, 4.77 Found: C, 77.72; H, 6.52; N, 4.82

EXAMPLE 13

$\beta$-[(2-Ethoxyethyl)amino]-$\alpha$-phenylbenzeneethanol.

A mixture of trans-stilbene oxide (1.96 g, 0.010 mol) and 2-ethoxyethylamine (2.67 g, 0.030 mol) was heated at 140° C. for 6 hours. After standing at ambient temperature for 10 hours, the solidified reaction mixture was triturated with isooctane and filtered to obtain a white solid (2.28 g, 80% yield) that was recrystallized from isooctane; mp 128°–130° C.

Analysis: Calculated for $C_{18}H_{23}NO_2$: C, 75.76; H, 8.12; N, 4.91 Found: C, 75.73; H, 8.20; N, 4.89

EXAMPLE 14

$\alpha$-Phenyl-$\beta$-[[2-(phenylmethoxy)propyl]amino]benzeneethanol.

A mixture of trans-stilbene oxide (1.96 g, 0.010 mol) and 2-benzyloxypropylamine (2.48 g, 0.015 mol) was heated at 140° C. for 6 hours and then allowed to stand at ambient temperature for 12 hours. The solidified reaction mixture was triturated with petroleum ether and filtered to obtain 2.72 g of a solid. Mass spectral analysis showed starting materials present. Recrystallization from isooctane gave 2.16 g (60%) of the product as a white solid; mp 114°–119° C.

Analysis: Calculated for $C_{24}H_{27}NO_2$: C, 79.74; H, 7.53; N, 3.87 Found: C, 79.53; H, 7.59; N, 3.92

EXAMPLE 15

$\alpha$-[[[2-(Phenylmethoxy)propyl]amino]methyl]benzenemethanol.

A mixture of styrene oxide (1.96 g, 0.010 mol) and 2-benzyloxypropylamine (2.48 g, 0.15 mol) was heated at 140° C. for 6 hours and then allowed to cool to ambient temperature and stand for 12 hours. The solidified reaction mixture was triturated with isooctane and filtered to obtain an impure solid that was recrystallized from isooctane to obtain 2.40 g of a white solid (84% yield); mp 90°–100° C. (undefined).

Analysis: Calculated for $C_{18}H_{23}NO_2$: C, 75.76; H, 8.12; N, 4.91 Found: C, 75.35; H, 8.08; N, 4.92

EXAMPLE 16

α-[[2-(2-Hydroxyethoxy)ethyl]amino]-α-phenylbenzeneethanol.

A mixture of trans-stilbene oxide (1.96 g, 0.010 mol) and 2-(2-aminoethoxy)ethanol (3.05 g, 0.030 mol) was heated at 140° C. for 6 hours. After standing at room temperature for 14 hours the reaction mixture was triturated with water, the solid product collected, and dried under ambient conditions for 3 days to obtain 2.77 g (92%) of material. The solid was recrystallized from methanol-isopropyl ether to obtain 1.89 g of the product; mp 140°–142° C.

Analysis: Calculated for $C_{18}H_{23}NO_3$: C, 71.73; H, 7.69; N, 4.65 Found: C, 71.73; H, 7.80; N, 4.68

EXAMPLE 17

β-[[3-(Hexyloxy)propyl]amino]-α-phenylbenzeneethanol.

A mixture of trans-stilbene oxide (1.96 g, 0.010 mol) and 3-hexyloxypropylamine (1.75 g, 0.011 mol) was heated at 140° C. for 6 hours. After standing at ambient temperature for 44 hours, the reaction mixture was dissolved in acetone (10 mL) and the solution poured into water (150 mL). The light brown oil that separated from solution solidified on standing for 1 hour. The solid was collected and dried on absorbent paper for 18 hours. The solid was then triturated in isooctane (soluble) and the solution chilled to obtain a solid that was collected, washed with cold isooctane, and dried under ambient conditions to obtain 1.20 g (34%) of the product; mp 67°–69° C.

Analysis: Calculated for $C_{23}H_{33}NO_2$: C, 77.70; H, 9.36; N, 3.93 Found: C, 77.75; H, 9.46; N, 3.99

EXAMPLE 18

β-[(2,2-Dimethoxyethyl)amino]-α-phenylbenzeneethanol.

A mixture of trans-stilbene oxide (1.96 g, 0.010 mol) and 2,2-dimethoxyethylamine (3.15 g, 0.030 mol) was heated in an oil bath at 140° C. for 5 hours. After standing at ambient temperature for 16 hours, the solid reaction mixture was triturated with isooctane and the white solid that remained was collected by filtration to obtain 2.15 g (71%) of the product. The product was recrystallized from toluene-isooctane; mp 147°–149° C.

Analysis: Calculated for $C_{18}H_{23}NO_3$: C, 71.73; H, 7.69; N, 4.65 Found: C, 71.79; H, 7.78; N, 4.69

EXAMPLE 19

α-Phenyl-β-[(tetrahydro-2H-pyran-2-ylmethyl)amino]benzeneethanol.

A mixture of trans-stilbene oxide (1.96 g, 0.010 mol) and 2-aminomethyltetrahydropyran (3.45 g, 0.030 mol) was heated in an oil bath at 140° C. for 6 hours. After standing at ambient temperature for 14 hours, the solidified reaction mixture was triturated with isooctane, and the tan solid collected by filtration to obtain 2.59 g (83% yield) of the product. The material was recrystallized from toluene-isooctane; mp 159°–163° C.

Analysis: Calculated for $C_{20}H_{25}NO_2$: C, 77.14; H, 8.09; N, 4.50 Found: C, 77.04; H, 8.15; N, 4.52

EXAMPLE 20

α-[[(2-Methoxyethyl)amino]methyl]benzenemethanol.

A mixture of styrene oxide (2.40 g, 0.020 mol) and 2-methoxyethylamine (4.50 g, 0.060 mol) was heated on a steam bath for 16 hours. After cooling to ambient temperature the oil began to crystallize. Trituration in isooctane followed by filtration gave a slightly impure solid. Recrystallization from isopropyl ether gave 1.52 g (39% yield) of the product; mp 77°–80° C.

Analysis: Calculated for $C_{11}H_{17}NO_2$: C, 67.66; H, 8.78; N, 7.17 Found: C, 67.42; H, 8.87; N, 7.15

EXAMPLE 21 erythro-β-[[3-(4-Morpholinyl)propyl]amino]-α-phenylbenzeneethanol.

A mixture of trans-stilbene oxide (1.96 g, 0.010 mol) and 4-(3-aminopropyl)morpholine (4.32 g, 0.030 mol) was heated in an oil bath at 140° C. for 2 hours. After standing at ambient temperature for 18 hours, the mixture was dissolved in methanol (20 mL). The solution was poured into water (150 mL) and upon standing a few minutes, a white solid appeared. The solid was collected by filtration and dried under ambient conditions to yield 2.44 g (72%) of the product. The solid was recrystallized from isooctane to yield 1.46 g; mp 128°–130° C.

Analysis: Calculated for $C_{21}H_{28}N_2O_2$: C, 74.08; H, 8.29; N, 8.23 Found: C, 73.94; H, 8.35; N, 8.16

EXAMPLE 22 erythro-β-[[3-(Methylthio)propyl]amino]-α-phenylbenzeneethanol.

A mixture of trans-stilbene oxide (1.96 g, 0.010 mol) and 3-methylthiopropylamine (3.15 g, 0.030 mol) was heated in an oil bath at 140° C. for 2 hours and the mixture then allowed to stand at ambient temperature for 18 hours. A white solid formed in the reaction mixture which was insoluble in methanol. The reaction mixture was triturated with methanol, and the insoluble solid was filtered to obtain the product (1.06 g, 35%); mp 124°–127° C.

Analysis: Calculated for $C_{18}H_{23}NOS$: C, 71.72; H, 7.69; N, 4.65 Found: C, 71.73; H, 7.77; N, 4.73

EXAMPLE 23 erythro-β-[[3-(1H-Imidazol-1-yl)propyl]amino]-α-phenylbenzeneethanol.

A mixture of trans-stilbene oxide (1.96 g, 0.010 mol) and 1-(3-aminopropyl)imidazole (3.75 g, 0.030 mol) was heated at 140° C. for 2 hours. After cooling, the mixture was dissolved in methanol (15 mL) and the solution poured into water (150 mL). After standing at room temperature for 70 hours, the aqueous layer was decanted, leaving a wet orange-red solid. The solid was dissolved in methylene chloride (50 mL), separated from the water layer, dried (MgSO_4) and concentrated to obtain a crude solid. The material was recrystallized from toluene-isooctane to obtain 0.97 g of the product as a tan solid (30%) which was vacuum dried in a drying pistol over refluxing toluene for 18 hours; mp 140°–142° C.

Analysis: Calculated for $C_{20}H_{23}N_3O$: C, 74.74; H, 7.21; N, 13.07

Found: C, 74.90; H, 7.18; N, 12.69

EXAMPLE 24

β-[[3-(4-Methyl-1-piperazinyl)propyl]amino]-α-phenylbenzeneethanol.

A mixture of trans-stilbene oxide (1.96 g, 0.010 mol) and 1-(3-aminopropyl)-4-methylpiperazine (1.57 g, 0.010 mol) was heated in an oil bath at 145° C. for 4 hours and allowed to stand at ambient temperature for 12 hours. The reaction mixture was dissolved in methanol (20 mL) and the solution poured into water (100 mL). A solid that formed on trituration in the water was collected by filtration and shown by nmr and mass spectral analyses to be trans-stilbene oxide (1.00 g). The solid was mixed with an additional 0.96 g of trans-stilbene oxide (0.0049 mol) and 3.14 g (0.020 mol) of 2-(3-aminopropyl)-4-methylpiperazine and the mixture was heated at 145° C. for 17 hours. The filtrate from which the trans-stilbene oxide was recovered was extracted with methylene chloride (2×20 mL) and the extract concentrated to an oil that crystallized on trituration with isooctane to yield 1.13 g of the product as an off-white solid.

The second reaction mixture was dissolved in methanol (15 mL), diluted with water (100 mL), and acidified with 6N hydrochloric acid solution. After washing with methylene chloride (50 mL) the aqueous layer was basified (6N sodium hydroxide solution) and extracted with methylene chloride (2×50 mL). The extract was dried (MgSO$_4$) and concentrated to an oil that gave the product as a tan solid upon trituration with isooctane (2.70 g). The total yield was 3.83 g (65%). After unsuccessful attempts to purify the free base by recrystallization, the remaining solid product was treated with a solution of anhydrous phosphoric acid in methanol to obtain the diphosphate salt; mp 223°–224° C. (decomposes).

Analysis: Calculated for $C_{22}H_{31}N_3O \cdot 2H_3PO_4$: C, 48.15; H, 6.79; N, 7.65 Found: C, 48.15; H, 6.85; N, 7.44

EXAMPLE 25

β-[[2-(Methylthio)ethyl]amino]-α-phenylbenzeneethanol.

A mixture of trans-stilbene oxide (1.18 g, 0.006 mol) and 2-(methylthio)ethylamine (0.78 g, 0.0085 mol) was heated at 140° C. in an oil bath for 15 hours. The cooled solid reaction mixture was triturated with isooctane and the red-brown solid collected. This was triturated with methanol-isopropyl ether giving an off-white solid (1.15 g, 67% yield); mp 163°–165° C.

Analysis: Calculated for $C_{17}H_{21}NOS$: C, 71.04; H, 7.36; N, 4.87 Found: C, 71.09; H, 7.40; N, 4.89

EXAMPLE 26

α-Phenyl-β-[1-(phenylmethyl)-4-piperidinylamino]-benzeneethanol.

A mixture of trans-stilbene oxide (1.96 g, 0.010 mol) and 4-amino-1-benzylpiperidine (5.70 g, 0.030 mol) was heated at 145° C. in an oil bath for 15 hours. The cooled mixture was then dissolved in methanol (20 mL) and the solution poured into water (200 mL). The product separated as an oil that solidified on standing. The solid was collected and dried under ambient conditions for 18 hours to obtain 3.68 g (95%) of material. Recrystallization from toluene-isooctane gave 2.31 g of the product as a tan solid; mp 128°–130° C.

Analysis: Calculated for $C_{26}H_{30}N_2O$: C, 80.79; H, 7.82; N, 7.25 Found: C, 80.41; H, 7.83; N, 7.26

EXAMPLE 27

The following Formula I compounds of this invention are disclosed as examples in U.S. Pat. No. 4,803,200.

a. 4-chloro-α-(4-chlorophenyl)-β-[(2-hydroxyethyl)amino]benzeneethanol erythro isomer.
b. β-[(2-hydroxyethyl)amino]-α-phenylbenzeneethanol erythro isomer.
c. 4-chloro-α-(4-chlorophenyl)-β-[(2-mercaptoethyl)amino]benzeneethanol.
d. β-[(2-mercaptoethyl)amino]-α-phenylbenzeneethanol.
e. α-[[(3-hydroxypropyl)amino]phenylmethyl]benzenemethanol erythro isomer.
f. β-[(2-hydroxypropyl)amino]-α-phenylbenzeneethanol.
g. β-[(2-methoxyethyl)amino]-α-phenylbenzeneethanol.
h. β-[(2-hydroxyethyl)methylamino]-α-phenylbenzeneethanol.
i. β-[(2-hydroxy-1-methylethyl)amino]-α-phenylbenzeneethanol.
j. α-[[(2-hydroxyethyl)amino]methyl]benzenemethanol.
k. β-[[3-(1-methylethoxy)propyl]amino]-α-phenylbenzeneethanol.
l. β-[[3-(2-methylpropoxy)propyl]amino]-α-phenylbenzeneethanol.
m. β-[(3-butoxypropyl)amino]-α-phenylbenzeneethanol.
n. β-[(2-methoxyethyl)amino]-α-phenylbenzeneethanol, threo isomer.
o. α-[[(tetrahydrofuran-2-ylmethyl)amino]methyl]benzenemethanol.
p. α-[[(5-hydroxypentyl)amino]phenylmethyl]benzenemethanol, erythro isomer.
q. α-[[(6-hydroxyhexyl)amino]phenylmethyl]benzenemethanol erythro isomer.
r. β-[(3-hydroxypropyl)amino]-4-methoxy-α-(4-methoxyphenyl)benzeneethanol.
s. β-[(5-hydroxypentyl)amino]-4-methoxy-α-(4-methoxyphenyl)benzeneethanol.
t. β-[(6-hydroxyhexyl)amino]-4-methoxy-α-(4-methoxyphenyl)benzeneethanol, erythro isomer.
u. β-[(4-hydroxybutyl)amino]-α-phenylbenzeneethanol, erythro isomer.
v. β-[(4-hydroxybutyl)amino]-4-methoxy-α-(4-methoxyphenyl)benzeneethanol.
w. β-[(2-hydroxyethyl)amino]-4-methoxy-α-(4-methoxyphenyl)benzeneethanol.
x. β-[(2-hydroxycyclohexyl)amino]-α-phenylbenzeneethanol.
y. β-[(2-hydroxyethyl)amino]-α-phenylbenzeneethanol.
z. 4-(dimethylamino)-β-[(2-hydroxyethyl)amino]-α-phenylbenzeneethanol.
aa. 4-chloro-α-(4-chlorophenyl)-β-[(2-hydroxyethyl)amino]benzeneethanol.
bb. β-[(2-hydroxyethyl)amino]-4-methyl-α-(4-methylphenyl)benzeneethanol.
cc. β-[(3-hydroxypropyl)amino]-4-methyl-α-(4-methylphenyl)benzeneethanol.

EXAMPLE 28

β,β'-[(2-Hydroxy-1,3-propanediyl)diimino]bis(α-phenylbenzeneethanol).

A mixture of trans-stilbene oxide (3.93 g, 0.020 mol) and 2-hydroxy-1,3-propanediamine (0.90 g, 0.010 mol) was heated on a steam bath for 18 hours, giving a white solid. The material was triturated with boiling toluene and allowed to cool. The white solid that formed was collected, washed with toluene, and dried under ambient conditions for 18 hours. The solid was then vacuum dried over refluxing toluene for 4 hours to obtain 2.60 g (55% yield); mp 155°–175° C. (undefined).

Analysis: Calculated for $C_{31}H_{34}N_2O_3$: C, 77.15; H, 7.10; N, 5.80 Found: C, 76.75; H, 7.21; N, 5.92

EXAMPLE 29

α,α',α"-[Nitrilotris(methylene)]trisbenzenemethanol.

A mixture of styrene oxide (2.40 g, 0.020 mol) and 2-amino-1-phenylethanol (4.11 g, 0.030 mol) was heated in an oil bath at 125° C. for 3 hours. The reaction mixture was cooled, dissolved in 15 mL of methanol, and the solution poured into 100 mL of water. The mixture was extracted with 2×75 mL portions of methylene chloride, the extracts combined, dried (magnesium sulfate) and concentrated to give a yellow oil that showed several products on tlc analysis. To purify, the oil was dissolved in methylene chloride (50 mL) and extracted with 2×50 mL portions of 1N HCl solution. A precipitate appeared in the methylene chloride layer which was collected and shown by mass spectral analysis to be the product. NMR analysis showed the solid to be the hydrochloride salt. The solid (0.48 g, 6% yield) was recrystallized from methanol-isopropyl ether; mp 206°-208° C. This compound is reported in Arch Pharm 293, 27-28 (1960) (CA 54:18417 g).

Analysis: Calculated for $C_{24}H_{27}NO_3 \cdot HCl$: C, 69.64; H, 6.82; N, 3.38 Found: C, 69.58; H, 7.06; N, 3.39

EXAMPLE 30

β,β'-[1,4-Butanediylbis(oxy)bis(1,3-propanediyl)bis-(imino)]bis-α-phenylbenzeneethanol.

A mixture of trans-stilbene oxide (3.92 g, 0.020 mol) and 1,12-diamino-4,9-dioxododecane (2.04 g, 0.010 mol) was heated in an oil bath at 140° C. for 6 hours. After standing at ambient temperature for 14 hours, the resultant glass was dissolved in toluene-isooctane on a steam bath. Upon cooling and trituration, a cream colored solid was obtained that was saturated with the solvent. The solid was dried in vacuo for 18 hours to yield 3.78 g (63%) of material. The solid was recrystallized from toluene-isooctane and vacuum dried in a drying pistol over refluxing ethanol for 4 hours; mp 109°-113° C.

Analysis: Calculated for $C_{38}H_{48}N_2O_4$: C, 76.48; H, 8.11; N, 4.69 Found: C, 76.07; H, 8.26; N, 4.85

EXAMPLE 31

2,2'-[Oxybis(ethanediyldiimino)]bis(1,2-diphenylethanol).

A mixture of trans-stilbene oxide (2.21 g, 0.0113 mol), 2-(2-aminoethoxy)ethylamine dihydrochloride (1 g, 0.00565 mol) and sodium bicarbonate (0.95 g, 0.0113 mol) were stirred together in n-butanol (10 mL) and heated on a steam bath for 16 hours. Upon cooling a solid formed. The mixture was triturated with methanol (25 mL) and the mixture then diluted with water (200 mL). The solid was collected and dried under ambient conditions on absorbent paper for 2 hours. The solid still had a strong odor of 1-butanol. The solid was heated in boiling toluene (50 mL) and isooctane (25 mL) added to the boiling solution. The organic layer was decanted from a small amount of a denser second layer, presumably water. Upon cooling, the product crystallized from the toluene-isooctane mixture. The solid was collected and dried under ambient conditions for 18 hours to obtain 2.05 g (92% yield); mp 161°-164° C.

Analysis: Calculated for $C_{32}H_{36}N_2O_3$: C, 77.39; H, 7.31; N, 5.64 Found: C, 77.40; H, 7.32; N, 5.77

EXAMPLE 32

β,β'-[1,4-Piperazinediylbis[3,1-propanediylbis-(imino)]bis-α-benzeneethanol.

A mixture of trans-stilbene oxide (3.92 g, 0.020 mol) and 1,4-bis(3-aminopropyl)piperazine (2.00 g, 0.010 mol) were heated together on a steam bath for 3 hours with no evidence of product formation. The mixture was then heated in an oil bath at 140° C. for 3 hours. After standing at ambient temperature for 15 hours, the reaction mixture was triturated with methanol (20 mL) and heated on a steam bath. A solid formed that was collected by filtration (after cooling) to obtain 1.73 g of a light tan solid. The solid was shown by nmr analysis to be the desired product (29% yield). The solid was triturated with boiling methanol, and the solid collected after the mixture had cooled. The solid was vacuum dried in a drying pistol over refluxing toluene for 20 hours; mp 189°-191° C.

Analysis: Calculated for $C_{38}H_{48}N_4O_2$: C, 76.99; H, 8.16; N, 9.45 Found: C, 76.75; H, 8.27; N, 9.78

EXAMPLE 33

β,β'-[Thiobis[2,1-ethanediylbis(imino)]]bis-α-phenylbenzeneethanol, trans isomer.

A mixture of trans-stilbene oxide (3.92 g, 0.020 mol) and bis-(3-aminopropyl)sulfide (1.20 g, 0.010 mol) was heated at 145° C. in an oil bath for 16 hours. The glassy product was triturated in boiling methanol to give a tan solid. The mixture was cooled to ambient temperature, and the solid collected by filtration. A second crop was obtained upon chilling the filtrate. Both crops were identical by tlc analysis (3% $NH_4OH$ in methanol). The combined solids (3.10 g, 60.5% yield) were recrystallized from acetone/water (2.09 g); mp 148°-150° C.

Analysis: Calculated for $C_{32}H_{36}N_2O_2S$: C, 74.96; H, 7.08; N, 5.46 Found: C, 74.70; H, 7.01; N, 5.45

EXAMPLE 34

β,β'-(1,3-Propanediyldiimino)bis-α-phenylbenzeneethanol.

A mixture of trans-stilbene oxide (3.92 g, 0.020 mol) and 1,3-propanediamine (0.74 g, 0.010 mol) was heated at 145° C. in an oil bath for 16 hours. After cooling, the reaction mixture was dissolved in methanol (20 mL) and the solution poured into water (100 mL). The water was decanted from the insoluble product which was then dissolved in warm methylene chloride and separated from a small amount of water. The methylene chloride solution was dried ($MgSO_4$) and concentrated to give 3.05 g (65%) of a glassy material. Trituration with acetone gave a cream colored solid. Petroleum ether was added to the mixture and the solid product collected (1.28 g). The solid was recrystallized from acetone and vacuum dried in a drying pistol over refluxing toluene for 15 hours; mp 152°-153° C.

Analysis: Calculated for $C_{31}H_{34}N_2O_2$: C, 79.79; H, 7.34; N, 6.00 Found: C, 79.40; H, 7.33; N, 6.00

EXAMPLE 35

β,β'-[Methyliminobis[3,1-propanediylbis(imino)]]bis-α-phenylbenzeneethanol.

A mixture of trans-stilbene oxide (3.92 g, 0.020 mol) and N,N-bis-(3-aminopropyl)-N-methylamine (1.45 g, 0.010 mol) was heated in an oil bath at 145° C. for 16 hours. After cooling to 100° C. the reaction mixture was dissolved in methanol (20 mL) and the solution poured into water (100 mL), giving an insoluble oil that solidified on standing at room temperature for several hours. The solid was collected and dried under ambient conditions to yield 5.70 g (100%) of material. The product was recrystallized from acetone/petroleum ether and then from toluene-isooctane, and vacuum dried at 40° C. for 15 hours; mp 108°–111° C.

Analysis: Calculated for $C_{35}H_{43}N_3O_2$: C, 78.18; H, 8.06; N, 7.81 Found: C, 78.29; H, 8.14; N, 7.51

EXAMPLE 36

$\beta,\beta',\beta''$-[Nitrilotris[2,1-ethanediyl]tris(imino)]tris-$\alpha$-phenylbenzeneethanol.

A mixture of trans-stilbene oxide (3.24 g, 0.0165 mol) and tris-(2-aminoethyl)amine (0.73 g, 0.005 mol) was heated in an oil bath at 145° C. for 15 hours. After cooling to ambient temperature the clear red-brown glass was dissolved in boiling methanol (75 mL). The hot methanol solution was poured into water (500 mL). The solution was acidified with 6N HCl solution and extracted with ether (100 mL). The aqueous solution was basified with 6N sodium hydroxide solution and extracted with methylene chloride (2×100 mL portions). The extract was washed with water (100 mL), dried (magnesium sulfate) and concentrated to give 3.84 g (100%) of a red-brown glassy material. To purify, the product was dissolved in acetone and excess ethereal hydrogen chloride solution added. Addition of isopropyl ether caused the salt to precipitate. The salt was collected and recrystallized from acetone-isopropyl ether to obtain the tetrahydrochloride salt dihydrate; melting began at 83° C., undefined above 83° C.

Analysis: Calculated for $C_{18}H_{54}N_4O_3 \cdot 4HCl \cdot 2H_2O$: C, 62.88; H, 6.82; N, 6.11 Found: C, 62.72; H, 6.94; N, 5.94

EXAMPLE 37

$\alpha,\alpha'$-[Thiobis[2,2'-ethanediylbis[nitrolobis(methylene)]]]bis-benzenemethanol.

A mixture of bis(2-aminoethyl)sulfide (2.40 g, 0.020 mol) and styrene oxide (16.00 g, 0.133 mol) was heated by an oil bath at 150° C. for 4 hours and then allowed to stand at ambient temperature for 12 hours. The mixture was triturated with petroleum ether and the solution decanted to remove unreacted styrene oxide. The trituration and decantation was repeated. High pressure liquid chromatographic analysis showed the insoluble material to consist of 3 products. An additional 16.00 g (0.133 mol) of styrene oxide was added and the mixture heated for another 4 hours at 150° C. The reaction mixture was triturated with petroleum ether as before. Thin layer chromatographic analysis (MeOH) on the insoluble portion showed 1 component. To isolate and purify, the oil was dissolved in ether (200 mL) and treated with excess ethereal HCl solution to obtain the solid dihydrochloride salt, mp undefined.

Analysis: Calculated for $C_{36}H_{44}N_2O_4S \cdot 2HCl$: C, 64.17; H, 6.89; N, 4.16 Found: C, 63.74; H, 7.02; N, 3.90

EXAMPLE 38

$\alpha,\alpha',\alpha'',\alpha'''$-[1,3-Propanediylbis[nitrilobis(methylene)]]tetrakisbenzenemethanol.

A mixture of styrene oxide 94.80 g, 0.040 mol) and 1,3-diaminopropane (0.74 g, 0.010 mol) was heated on a steam bath for 18 hours. To isolate and purify, the viscous oil was dissolved in methanol (20 mL) and treated with a solution of anhydrous phosphoric acid (1.96 g, 0.020 mol) in methanol (20 mL). Addition of isopropyl ether caused the salt to separate from solution as an oil. The solvent was allowed to evaporate, leaving a solid (4.20 g, 56% yield). The solid was triturated with hot ethanol, the mixture cooled, and the insoluble product was collected by vacuum filtration and dried under ambient conditions for 4 days to obtain the monohydrate of the diphosphate salt; mp 205°–210° C. (decomposes).

Analysis: Calculated for $C_{35}H_{50}N_2O_{13}P_2$: C, 54.69; H, 6.56; N, 3.64 Found: C, 54.79; H, 6.40; N, 3.61

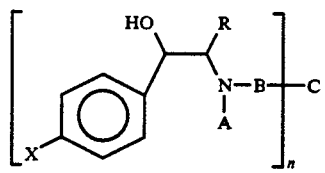

| Ex | R | X | A | B | n | C |
|---|---|---|---|---|---|---|
| 1 | $C_6H_5$ | H | H | $-CH_2-$ | 1 | $-CO_2C_2H_5$ |
| 2 | $C_6H_5$ | H | H | $-\underset{\underset{-CH_2OH}{\mid}}{\overset{\overset{CH_3}{\mid}}{C}}-CH_2-$ | 1 | $-OH$ |
| 3 | $C_6H_5$ | H | H | $-CH_2-\underset{\underset{OH}{\mid}}{CH}-CH_2-$ | 1 | $-OH$ |
| 4 | $C_6H_5$ | H | H | $-CH_2-\underset{\underset{CH_2OH}{\mid}}{CH}-CH_2CH_2-$ | 1 | $-OH$ |
| 5 | $C_6H_5$ | H | H | $-CH_2-\underset{\underset{OH}{\mid}}{CH}-CH_2-$ | 1 | $-NEt_2$ |

-continued

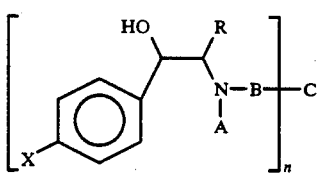

| Ex | R | X | A | B | n | C |
|---|---|---|---|---|---|---|
| 6 | $C_6H_5$ | H | | $-CH_2-CH(OH)-CH_2CH_2-$ | 1 | $-N\underset{\smile}{\frown}O$ (morpholino) |
| 7 | $C_6H_5$ | H | H | $-CH(CH_2OH)-$ | 1 | $-CH(OH)C_6H_5$ |
| 8 | $C_6H_5$ | H | H | $-CH_2$ | 1 | $-CH(OH)C_6H_5$ |
| 9 | $C_6H_5$ | H | | cyclohexyl | 1 | $-C(OH)(C_6H_4F)_2$ |
| 10 | $C_6H_5$ | H | H | $CH_2-$ | 1 | tetrahydrofuranyl |
| 11 | $C_6H_5$ | H | H | $-(CH_2)_3-$ | 1 | $-OCH_2CH_2OCH_2CH_3$ |
| 12 | $C_6H_5$ | H | H | $-CH_2-$ | 1 | furanyl |
| 13 | $C_6H_5$ | H | H | $-CH_2CH_2-$ | | $-OCH_2CH_3$ |
| 14 | $C_6H_5$ | H | H | $-CH_2CH_2-CH_3$ (with $CH_3$ branch) | 1 | $-OCH_2C_6H_5$ |
| 15 | H | H | H | $-CH-CH(CH_3)-$ | 1 | $-OCH_2C_6H_5$ |
| 16 | $C_6H_5$ | H | H | $-CH_2-CH_2$ | 1 | $-O-CH_2CH_2OH$ |
| 17 | $C_6H_5$ | H | H | $-CH_2CH_2CH_2-$ | 1 | $-O-C_6H_{13}$ |
| 18 | $C_6H_5$ | H | H | $-CH_2-$ | 1 | $-CH(OCH_3)_2$ |
| 19 | $C_6H_5$ | H | H | $-CH_2-$ | 1 | tetrahydropyranyl |
| 20 | H | H | H | $-CH_2CH_2-$ | 1 | $-OCH_3$ |
| 21 | $C_6H_5$ | H | H | $-CH_2CH_2CH_2-$ | 1 | morpholino |
| 22 | $C_6H_5$ | H | H | $-CH_2CH_2CH_2-$ | 1 | $-SCH_3$ |
| 23 | $C_6H_5$ | H | H | $-CH_2CH_2CH_2-$ | 1 | imidazolyl |
| 24 | $C_6H_5$ | H | H | $-CH_2CH_2CH_2-$ | 1 | N-methylpiperazinyl |

-continued

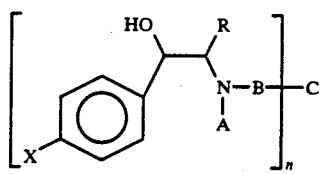

| Ex | R | X | A | B | n | C |
|---|---|---|---|---|---|---|
| 25 | $C_6H_5$ | H | H | $-CH_2CH_2-$ | 1 | $-SCH_3$ |
| 26 | $C_6H_5$ | H | H | — | 1 | (4-benzylpiperidin-1-yl) |
| 27a | $4-ClC_6H_5$ | 4-Cl | H | $-CH_2CH_2-$ | 1 | $-OH$ |
| 27b | $C_6H_5$ | H | H | $-CH_2CH_2-$ | 1 | $-OH$ |
| 27c | $4ClC_6H_5$ | 4-Cl | H | $-CH_2CH_2-$ | 1 | $-SH$ |
| 27d | $C_6H_5$ | H | H | $-CH_2CH_2-$ | 1 | $-SH$ |
| 27e | $C_6H_5$ | H | H | $-CH_2CH_2CH_2-$ | 1 | $-OH$ |
| 27f | $C_6H_5$ | H | H | $-CH_2CH_2-$ with $CH_3$ branch | 1 | $-OH$ |
| 27g | $C_6H_5$ | H | H | $-CH_2CH_2-$ | 1 | $-OCH_3$ |
| 27h | $C_6H_5$ | H | $CH_3$ | $-CH_2CH_2-$ | 1 | $-OH$ |
| 27i | $C_6H_5$ | H | H | $-CH-CH_2$ with $CH_3$ branch | 1 | $-OH$ |
| 27j | H | H | H | $-CH_2CH_2-$ | 1 | $-OH$ |
| 27k | $C_6H_5$ | H | H | $-CH_2CH_2CH_2-$ | 1 | $-O-CH(CH_3)_2$ (isopropoxy) |
| 27l | $C_6H_5$ | H | H | $-CH_2CH_2CH_2-$ | 1 | $-O-CH_2-CH(CH_3)_2$ (isobutoxy) |
| 27m | $C_6H_5$ | H | H | $-CH_2CH_2CH_2-$ | 1 | $-OC_4H_9$ |
| 27n | $C_6H_5$ | H | H | $-CH_2CH_2$ | 1 | $-OCH_3$ |
| 27o | H | H | H | $-CH_2-$ | 1 | (tetrahydrofuran-2-yl) |
| 27p | $C_6H_5$ | H | H | $-(CH_2)_5-$ | 1 | $-OH$ |
| 27q | $C_6H_5$ | H | H | $-(CH_2)_6-$ | 1 | OH |
| 27r | $4-CH_3OC_6H_4-$ | $4-OCH_3$ | H | $-CH_2CH_2CH_2-$ | 1 | $-OH$ |
| 27s | $4-CH_3OC_6H_4-$ | $4-OCH_3$ | H | $-(CH_2)_5-$ | 1 | $-OH$ |
| 27t | $4-CH_3OC_6H_4-$ | $4-OCH_3$ | H | $-(CH_2)_6-$ | 1 | $-OH$ |
| 27u | $C_6H_5$ | H | H | $-(CH_2)_4-$ | 1 | $-OH$ |
| 27v | $4-CH_3OC_6H_4-$ | $4-OCH_3$ | H | $-(CH_2)_4-$ | 1 | $-OH$ |
| 27w | $4-CH_3OC_6H_4-$ | $4-OCH_3$ | H | $-CH_2CH_2-$ | 1 | $-OH$ |
| 27x | $C_6H_5$ | H | H | — | 1 | (2-methylcyclohexan-1-ol) |
| 27y | $C_6H_5$ | H | H | $-CH_2CH_2-$ | 1 | $-OH$ (threo isomer) |
| 27z | $4-Me_2NC_6H_4-$ | H | H | $-CH_2CH_2-$ | 1 | $-OH$ |
| 27aa | $4-ClC_6H_4$ | 4-Cl | H | $-CH_2CH_2CH_2-$ | 1 | $-OH$ |
| 27bb | $4-CH_3C_6H_4-$ | $4-CH_3$ | H | $-CH_2CH_2-$ | 1 | $-OH$ |
| 27cc | $4-CH_3C_6H_4-$ | $4-CH_3$ | H | $-CH_2CH_2CH_2-$ | 1 | $-OH$ |
| 28 | $C_6H_5$ | H | H | $-CH_2-$ | 2 | $-CH(OH)-$ |
| 29 | $C_6H_5$ | H | $-CH_2CHC_6H_5$ with OH | $-CH_2$ | 1 | $-CH(OH)C_6H_5$ |

-continued

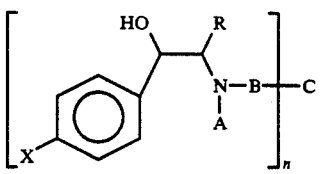

| Ex | R | X | A | B | n | C |
|---|---|---|---|---|---|---|
| 30 | $C_6H_5$ | H | H | $-CH_2CH_2CH_2-$ | 2 | $-O-(CH_2)_4-O-$ |
| 31 | $C_6H_5$ | H | H | $-CH_2CH_2-$ | 2 | $-O-$ |
| 32 | $C_6H_5$ | H | H | $-CH_2CH_2CH_2-$ | 2 | ⟨N   N−⟩ (piperazine) |
| 33 | $C_6H_5$ | H | H | $-CH_2CH_2-$ | 2 | $-S-$ |
| 34 | $C_6H_5$ | H | H | — | 2 | $-CH_2CH_2CH_2-$ |
| 35 | $C_6H_5$ | H | H | $-CH_2CH_2CH_2-$ | 2 | $-N(CH_3)-$ |
| 36 | $C_6H_5$ | H | H | $-CH_2CH_2-$ | 3 | $>N-$ |
| 37 | H | H | $-CH_2CHC_6H_5$ with OH | $-CH_2CH_2-$ | 2 | $-S-$ |
| 38 | H | H | $-CH_2CHC_6H_5$ with OH | — | 2 | $-CH_2CH_2CH_2-$ |

Pharmacology

Method 1. Duodenal Ulceration in Rats

This procedure is based on the method of Kurebayashi et al. 1984 Arch. Int. Pharmacodyn. 271: 155-168. Mature male Sprague-Dawley rats are fasted overnight with water allowed ad libitum. On the day of the study they are weighed and randomized by weight into control, reference and treatment groups. All rats are dosed orally with a preparation of Dulcerozine (200 mg/kg) and Meperizole (100 mg/kg) in 5.0% acacia solution (8 ml/kg) using a 3-inch stainless steel oral dosing needle and syringe. This combination given orally was found to be more effective and gave less variable results than when Dulcerozine was used alone and administered subcutaneously at a dose of 300 mg/kg. One hour after administration of the Dulcerozine/Meperizole preparation, the test group of rats are dosed orally with test compound (3.16, 10, 31.6, or 100 mg/kg). The reference group of rats are given atropine sulfate (10 mg/kg) or Sucralfate (500 mg/kg). The control group of rats is given 0.5% carboxymethylcellulose solution (8 ml/kg). Test and reference compounds are dissolved or suspended in deionized water or 0.5% carboxymethylcellulose in deionized water in a volume of 8 ml/kg. All rats are dosed again 7 hours after being given the Dulcerozine/Meperizole preparation.

After 18 hours the rats are sacrificed by cervical dislocation. The stomach and a 3-cm length of the duodenum is removed, opened along the mesenteric border, and rinsed with tepid tap water. The duodenum is examined macroscopically with a 3.75× magnifying lamp and each duodenal ulcer scored to determine the ulcer index. The ulcer index represents the sum of the product(s) of the length times width of the ulcer times the severity factor (1=shallow ulcer, 3=deep or penetrated ulcer). The ulcer indices are analyzed statistically by means of the Dunnett's t-test (Dunnett, C.W. 1955, J. Am. Stat. Assoc. 50:1096-1121) using a 1-tailed test ($p<0.5$). Where the ulcer indices are widely variable, the square roots of the ulcer indices are used for statistical analysis. The percent change is determined in comparison to the controls.

Method 2. Gastric Ulceration in Rats

The procedure used is essentially that described by A. Robert, Gastroenterology 77:761-767 (1979). Mature male Sprague-Dawley rats are fasted overnight prior to the start of the experiment. The animals are weighed and randomized by weight into control, reference and treatment groups. Each animal is dosed orally or intraperitoneally (4 ml/kg) with either test article (3.16, 10, 31.6 or 100 mg/kg), reference article (carbenoxolone, 100 mg/kg) or control (vehicle). The test article or reference article articles are dissolved or suspended in deionized water or 0.5% carboxymethylcellulose solution in deionized water for dosing at the rate of 4 ml/kg. After 30 minutes, each rat is given 1 ml of absolute ethanol orally by means of a 3-inch stainless steel oral dosing needle. Sixty minutes after receiving ethanol, each rat is killed by cervical dislocation, the stomach removed and cut open along the lesser curvature. The stomachs are rinsed with tap water and stretched open for damage assessment. Gastric damage is assessed in each stomach by use of an arbitrary scoring index wherein the degree of damage is an approximation of the percent of the stomach that is involved in the damage. The score is reported in increments of 5% to a maximum score of 50%. Dunnett's T-Test (Dunnett, C.W. 1955. J. Am. Stat. Assoc. 50:1096–1121) is used to determine statistical significance between control and treated groups.

TABLE II

Pharmacological Data for Formula I Compounds
Gastrointestinal Injury
(% change in ulcer index)[1]

| Example | Duodenal (Method 1) | Gastric (Method 2) |
|---|---|---|
| 1 | | −33/31.6 |
| 2 | | −17/31.6 |
| 3 | | −33/31.6 |
| 4 | | −30/31.6 |
| 5 | | −17/31.6 |
| 6 | | −8/31.6 |
| 7 | −21/31.6 | |
|   | −54/31.6 | −67/31.6 |
| 8 | +4/31.6 | −59/31.6 |
| 9 | | −14/31.6 |
| 10 | +51/100 | −62/31.6 |
| 11 | | −43/31.6 |
| 12 | +27/31.6 | |
| 13 | +78/31.6 | −50/31.6 |
| 14 | −30/100 | −79/31.6 |
| 15 | −45/100 | −81/31.6 |
| 16 | −12/100 | 54/31.6 |
| 17 | −58/100 | −100/31.6 |
| 18 | | −39/31.6 |
| 19 | +6/100 | −62/31.6 |
| 20 | +33/100 | −97/31.6 |
| 21 | | −46/31.6 |
| 22 | −84/100 | −59/31.6 |
| 23 | | −43/31.6 |
| 25 | | −21/31.6 |
| 26 | . | −8/31.6 |
| 27a | −44/100 | −94/31.6 |
| 27b | −65/100 | −43/31.6 |
| 27c | −84/100 | −100/31.6 |
| 27d | −40/100 | −39/31.6 |
| 27e | | −5/31.6 |
| 27f | | −28/31.6 |
| 27g | | −15/31.6 |
| 27h | | −12/31.6 |
| 27i | | −28/31.6 |
| 27j | +52/31.6 | −75/31.6 |
| 27k | −31/100 | −75/31.6 |
| 27l | −40/100 | −69/31.6 |
| 27m | −68/100 | −72/31.6 |
| 27n | +16/31.6 | −44/31.6 |
| 27o | | −29/31.6 |
| 27p | | −5/31.6 |
| 27q | | −20/31.6 |
| 27r | | −8/31.6 |
| 27s | | −10/31.6 |
| 27t | +32/100 | +3/31.6 |
| 27u | | −8/31.6 |
| 27v | | −38/31.6 |
| 27w | | −21/31.6 |
| 27x | | −27/31.6 |
| 27y | | −23/31.6 |
| 27z | | −25/31.6 |
| 27aa | −62/100 | −100/31.6 |
| 27bb | | −70/31.6 |
| 27cc | | −54/31.6 |
| 28 | −70/100 | −79/31.6 |
| 29 | | −63/31.6 |
| 30 | −42/31.6 | −61/10 |
|   | −79/100 | −100/31.6 |
| 31 | −49/10 | |
|   | −66/31.6 | |
|   | −76/100 | −37/10 |
|   |  | −96/31.6 |
| 32 | −97/100 | −62/31.6 |
| 33 | −19/100 | −79/31.6 |
| 34 | −99/100 | −100/31.6 |
| 35 | −84/100 | −62/31.6 |
| 36 | −100/100 | −98/31.6 |

TABLE II-continued

Pharmacological Data for Formula I Compounds
Gastrointestinal Injury
(% change in ulcer index)[1]

| Example | Duodenal (Method 1) | Gastric (Method 2) |
|---|---|---|
| 38 | +40/31.6 | −27/31.6 |

[1] % change from control/dose (mg/kg,PO)

PHARMACEUTICAL COMPOSITIONS AND ADMINISTRATION

The invention further provides for pharmaceutical compositions for administering to a warm-blooded animal a dosage form comprising at least one of the compounds according to the invention in association with a pharmaceutical carrier or excipient for oral, parenteral or rectal administration. Thus, for example, compositions for oral administration are preferable solids and can take the form of capsules, tablets or coated tablets. Suitable excipients for these solid dosage forms include lactose, potato and maize starches, talc, gelatin, stearic acid, silicic acid, magnesium stearate and polyvinyl pyrrolidine. Oral liquid dosage forms can be in the form of solutions, suspensions or emulsions comprized of a Formula I compound in a suitable liquid carrier, for example, water, sugar syrup, propylene glycol, glycerine, ethanol and the like. For parenteral administration, the carrier or excipient can be a sterile parenterally acceptable liquid, for example, water or arachis oil. In compositions for rectal administration the carrier can comprise a suppository base, for example, cocoa butter or a glyceride.

Advantageously, the compositions are formulated as dosage units, each unit being adapted to supply a fixed dose of active ingredient. Tablets, capsules or coated tablets are examples of the preferred dosage form. It is only necessary that the active ingredient constitute an effective amount such that a suitable effective dosage will be consistent with the dosage form employed.

Multiple doses may be given to obtain the desired therapeutic effect. The exact individual doses will, of course, be determined according to standard medical principles under the direction of a physician or veterinarian. Generally, the following guide to projected human doses is derived by knowledge of the activity obtained in animal screening tests in the method of the invention compared to activity of known agents in the field in the same animal tests. However, the amount of the active compounds administered need not be limited by these comparisons due to uncertainty in transposing comparative animal data to human treatment.

The projected antiulcer dose for the compounds of this invention is from 0.3 to 1000 mg/kg daily and may be given in divided doses two to four times daily, for example, unit dosage forms containing 0.1 to 300 mg/kg given 2 to 4 times each day.

The active ingredients of the invention may be combined with other pharmacologically active agents, buffers, antacids, demulcents and the like for administration and the proportions of the active agent in the composition may vary widely.

Various modifications and equivalents will be apparent to one skilled in the art and may be made in the compounds, methods and pharmaceutical compositions of the present invention without departing from the spirit and scope thereof, and it is understood that the

We claim:
1. A compound according to the formula:

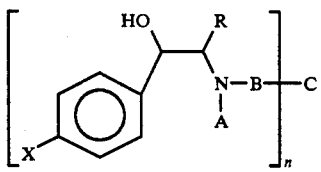

wherein X is H, —Cl, —CH$_3$ or —OCH$_3$;
A is —H, —CH$_3$ or

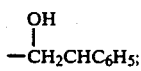

n is 2;
B is C$_1$-C$_6$ alkylene, optionally substituted with —OH, —CH$_2$OH or —CH$_3$;
C is a linking group selected from the group consisting of —O—(CH$_2$)$_{2-6}$—O—, —O—, —S—, or

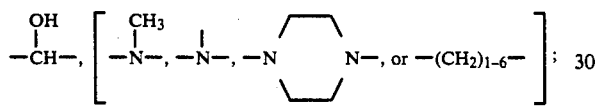

R is H or

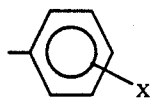

where X is as defined above;
a diastereomer, or a pharmaceutically acceptable salt thereof.

2. A compound according to claim 1 which is selected from the group consisting of:
β,β'-[1,4-butanediylbis(oxy)bis(1,3-propanediyl)bis-(imino)]bis-α-phenylbenzeneethanol,
2,2'-[oxybis(ethanediyldiimino)]bis(1,2-diphenylethanol),
β,β'-[thiobis[2,1-ethanediylbis(imino)]]bis-α-phenylbenzeneethanol, or a pharmaceutically acceptable salt thereof.

3. A pharmaceutical composition for the treatment of gastric and duodenal ulcers comprised of:
a. A therapeutically effective amount of a compound according to the formula:

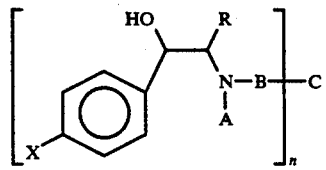

wherein X is H, —Cl, —CH$_3$, or —OCH$_3$;
A is H, —CH$_3$ or

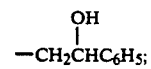

n is 2;
B is C$_1$-C$_6$ alkylene, optionally substituted with —OH, —CH$_2$OH, or —CH$_3$;
C is a linking group selected from the group consisting of

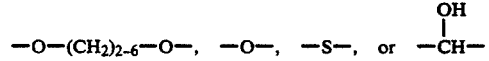

a diastereomer, or a pharmaceutically acceptable salt thereof and
b. a pharmaceutical carrier.

4. A method of treatment or gastric or duodenal ulceration in warm-blooded animals which comprises administering thereto a therapeutically effective amount of a compound of the formula:

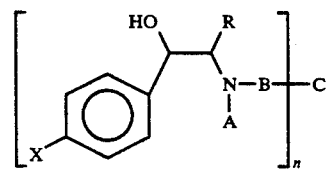

wherein X is H, —Cl, —CH$_3$ or —OCH$_3$;
A is —H, —CH$_3$ or

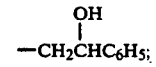

n is 2 to 3;
B is C$_1$-C$_6$ alkylene, optionally substituted with —OH, —CH$_2$OH or —CH$_3$;
C is a linking group selected from the group consisting of —O—(CH$_2$)$_{2-6}$—O—, —O—, —S—,

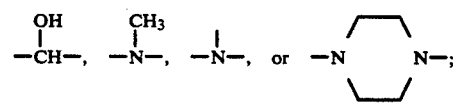

R is H or

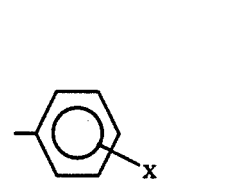

where X is as defined above;
a diastereomer, or a pharmaceutically acceptable salt thereof.

5. The method of treatment according to claim 4 wherein the compound used is selected from the group consisting of:
β,β'-[2-hydroxy-1,3-propanediyl)diimino]bis-α-phenylbenzeneethanol
β,'-[1-4-butanediylbis(oxy)bis(1,3-propanediyl)bis-(imino)]bis-α-phenylbenzeneethanol, 2,2'-[oxybis(ethanediyldiimino)]bis(1,2-diphenylethanol), β,β'-(1,4-piperazinediylbis[3,1-propanediylbis(imino)]bis-a-benzeneethanol β,β'-[thiobis[2,1-ethanediylbis(imino)]]bis-α-phenylbenzeneethanol, β,β'-(1,3-propanediyldiimino)bis-α-phenylbenzeneethanol β,β'-[methyliminobis[3,1-propanediylbis(imino)]]bis-a-phenylbenzeneethanol β,β',β''-[nitrilotris-[2,1-ethanediyl]tris(imino)]tris-a-phenylbenzenethanol, or a pharmaceutically acceptable salt thereof.

* * * * *